(12) United States Patent
Ashraf

(10) Patent No.: US 6,197,039 B1
(45) Date of Patent: Mar. 6, 2001

(54) TRIPLE POINTED MICRO KNIFE

(76) Inventor: Bahman Ashraf, 120 Wood Ave. South, Suite 305, Iselin, NJ (US) 08830

( * ) Notice: Subject to any disclaimer, the term of this patent is extended or adjusted under 35 U.S.C. 154(b) by 0 days.

(21) Appl. No.: 09/457,954

(22) Filed: Dec. 9, 1999

(51) Int. Cl.$^7$ .................................................. A61B 17/32
(52) U.S. Cl. .......................... 606/172; 606/183; 606/187; 606/167
(58) Field of Search ..................................... 606/167, 131, 606/132, 133, 181, 183, 185–187, 172; 433/144; 30/169, 172, 273, 286, 226, 287, 299, 304–305, 278

(56) References Cited

U.S. PATENT DOCUMENTS

| | | | |
|---|---|---|---|
| 4,717 | * | 8/1846 | Ahrens ................................. 606/183 |
| 5,111 | * | 5/1847 | Leypoldt ............................. 606/183 |
| 8,095 | * | 5/1851 | Leypoldt ............................. 606/183 |
| 3,358,688 | * | 12/1967 | Tanner ................................. 606/132 |
| 3,613,242 | * | 10/1971 | Hill et al. ............................. 30/295 |
| 4,417,580 | * | 11/1983 | Birchmeier . |
| 5,217,476 | * | 6/1993 | Wishinsky ........................... 606/167 |
| 5,250,067 | * | 10/1993 | Gelfer . |
| 5,611,810 | * | 3/1997 | Arnold ................................. 606/167 |
| 5,782,851 | * | 7/1998 | Rassman ............................. 606/133 |
| 5,858,019 | * | 1/1999 | Ashraf . |
| 5,922,000 | * | 7/1999 | Chodorow ........................... 606/167 |
| 5,989,273 | * | 11/1999 | Arnold ................................. 606/167 |
| 6,030,404 | * | 2/2000 | Lawson et al. ..................... 606/186 |
| 6,083,196 | * | 7/2000 | Trautman et al. ................... 604/46 |

* cited by examiner

Primary Examiner—Michael H. Thaler
Assistant Examiner—Kristen Droesch

(57) ABSTRACT

A surgical implement employs first, second and third like elongated thin vertical closely spaced apart cutting blades. Each blade terminates at its upper end in an arrow head type point. All of these points lie in a common horizontal plane. Connection apparatus is integral with and forms a common base with the lower ends of all of these blades.

3 Claims, 1 Drawing Sheet

TRIPLE POINTED MICRO KNIFE

BACKGROUND OF THE INVENTION

As explained in U.S. Pat. No. 5,858,019, in order to implant hair elements into bald regions of the scalp of a patient, the hair elements are removed from other portions of the body of the patient and are surgically implanted into extremely small openings previously cut into the bald regions. This patent discloses a combination of overlying interconnected layers with a plurality of surgical cutting units imbedded in these layers in spaced apart positions. Each unit has a plurality of knife elements. These elements have downwardly extending cutting points. When the patented device is disposed for use in engagement with a selected portion of the scalp of a patient, the surgeon presses down upon the top most layer and causes the points of the knife elements to engage the selected portion of the scalp.

However, the patented device has a large number of knife elements and is used to treat a corresponding large portion of the scalp. In many implant operations, it is necessary to implant hair elements into a small scalp area which is much too small to be implanted using the patented device. The present invention is directed toward a new type of surgical implement which can be used in the implant operations utilizing a small scalp area. This implement can be used for cutting three extremely small closely spaced openings simultaneously in the scalp.

Other objects and advantages of this invention will either be explained or will become apparent hereinafter.

SUMMARY OF THE INVENTION

In accordance with the principles of this invention, the surgical implement utilizes first, second and third like elongated thin vertical closely spaced apart cutting blades. Each blade terminates at its upper end in an arrow head type point. All of these points lie in a common horizontal plane. A horizontal base member is disposed below the lower ends of the blades. The member has three vertically upwardly extending extensions, each of which is integral with the lower end of each corresponding blade.

A vertical hollow handle can be disposed below the base member, with the base member being disposed within the upper end of the handle and the blades extending outwardly from the upper end of the handle at right angles to the handle and member. The width of each blade between the arrow head and the corresponding extension is no larger than the maximum width of the arrow head. The width of each extension is larger than the maximum width of the of the arrow head.

In use the surgeon grasps the handle and presses the blades via their arrow heads into the scalp of the patient until the lower ends of the blades are prevented from entering the scalp because the vertical extensions block further entry. In this manner three small closely spaced openings are cut into the scalp so that the hair implant process can be continued.

DETAILED DESCRIPTION OF PREFERRED EMBODIMENTS

Figure 1:
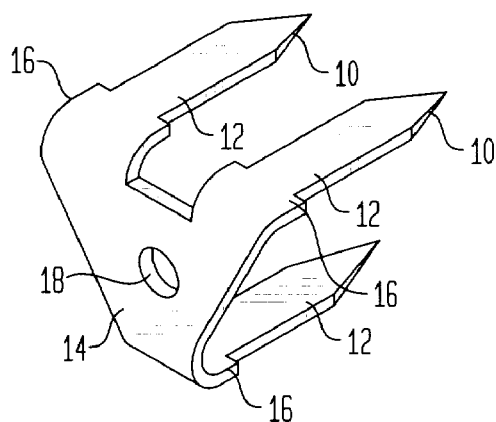
FIG. 1 is a perspective view of the blades and supporting means.
Figure 2:
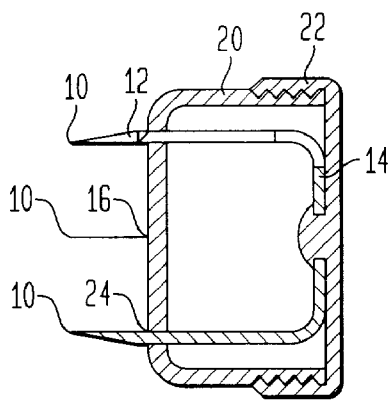
FIG. 2 is a cross sectional view of a handle, blades and supporting means using the structure of FIG. 1.
Figure 4:
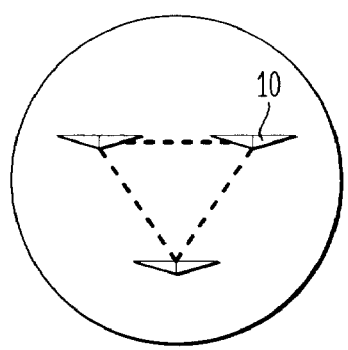
FIG. 4 is a view taken along line 4—4 in FIG. 3.

All parts shown in the drawings are made of surgical steel. Referring now to FIG. 1, first, second and third elongated thin vertical equidistantly spaced cutting blades each terminate at its upper end with an arrow head type point 10. The points of all these heads lie in a common horizontal plane. In one application, these blades each have a thickness of about 0.1 mm and are spaced apart by a distance of about 3.0 mm. Consequently, as shown in FIG. 4, the arrow head points define the vertices of an equilateral triangle. The bodies of each blade as shown at 12 are no wider than the maximum width of the arrow heads. In this application, the maximum width of each arrow head is about 1.5 mm. Two of the blades lie in a common vertical plane while the third blade lies in a parallel vertical plane spaced from the common vertical plane.

A flat horizontal base plate 14 is disposed below the blades and has three spaced apart vertical extensions 16 each of which is integral with the lower end of the corresponding blade. Each extension is wider than the maximum width of the corresponding arrow head. In this application, the width of each extension is about 2.0 mm and its thickness can be larger than 0.1 mm.

When the blades are used to cut into the scalp, each blade including the body and the arrow head penetrate the scalp of a depth of 5 or 6 mm. The connection of the body to the extension enables the extension to form a stop and limit the depth of cut.

Figure 3:
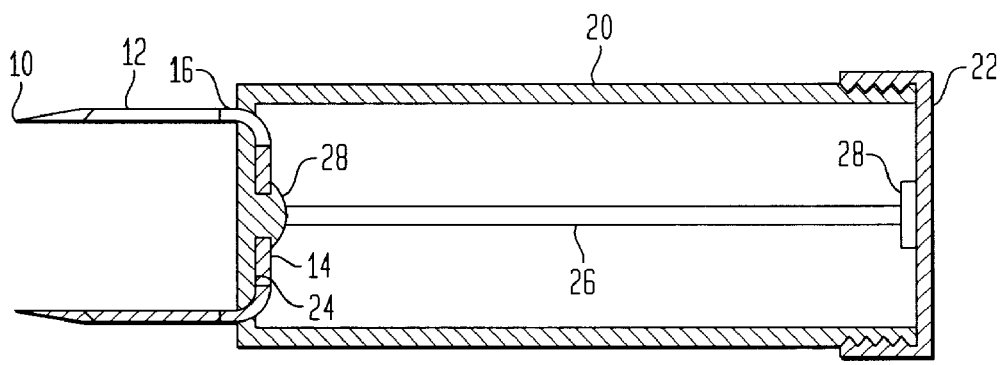
FIG. 3 is a view similar to FIG. 2 but illustrating a modification thereof.

Depending upon the type of holder or handle employed, the plate 14 may or may not have a central hole 18. FIG. 3 shows a holder using the plate with a hole. A hollow cylinder 20 has an open end closed by a screw type cap 22 and an opposite end which is solid except for three small openings 24 which accommodate the blades and extensions. The plate 14 is held in position within and bearing against the opposite end.

FIG. 4 shows a holder using a plate without a hole. Cylinder 20 has an open end closed by screw type cap and an opposite end which is solid except for the three small openings 24 which accommodate the blades and extensions. The plate 14 is held in position as before. However, an elongated rod 26 disposed axially within the cylinder has enlargements 28 at each end. One end bears against the plate and the other end is held in position by the cap.

While the invention has been explained with particular reference to the drawing and description of preferred embodiments, the protection solicited is to be limited only by the terms of the claims which follow.

What is claimed is:

1. A surgical implement comprising:
   first, second and third like elongated thin vertical closely spaced apart cutting blades which arc equidistantly spaced apart, the first and second blades lying in a first common vertical plane, the third blade lying in a second vertical plane spaced from and parallel to said first plane;
   each blade having a central longitudinal axis and terminating at its upper end in a point located on said longitudinal axis, each point being located at the apex of two converging straight edges of the blade, all of said points lying in a common horizontal plane and defining the vertices of an equilateral triangle; and
   means integral with and forming a common base with the lower ends of all of said blades, said means including a horizontal plate and first, second and third upwardly extending vertical extensions, each extension being integral with the lower end of the corresponding blade, said first, second, and third blades being the only blades on said surgical implement.

2. The implement of claim 1 wherein the width of each extension is larger than the maximum width of the arrow head.

3. The implement of claim 2 further including a vertically elongated hollow handle extending below the horizontal plate, the plate being secured within the upper end of the handle and the blades extending outwardly from the upper end ol the handle.

* * * * *